(12) United States Patent
Shieu et al.

(10) Patent No.: US 11,752,225 B2
(45) Date of Patent: Sep. 12, 2023

(54) SYSTEMS AND METHODS FOR PRODUCING STERILE INJECTION DEVICES

(71) Applicant: COHERUS BIOSCIENCES, INC., Redwood City, CA (US)

(72) Inventors: Wendy Shieu, Redwood City, CA (US); Gerald Llorach, Redwood City, CA (US)

(73) Assignee: Coherus BioSciences, Inc., Redwood City, CA (US)

( * ) Notice: Subject to any disclaimer, the term of this patent is extended or adjusted under 35 U.S.C. 154(b) by 0 days.

(21) Appl. No.: 17/998,818

(22) PCT Filed: May 21, 2021

(86) PCT No.: PCT/US2021/033657
§ 371 (c)(1),
(2) Date: Nov. 15, 2022

(87) PCT Pub. No.: WO2021/237091
PCT Pub. Date: Nov. 25, 2021

(65) Prior Publication Data
US 2023/0201387 A1    Jun. 29, 2023

Related U.S. Application Data

(60) Provisional application No. 63/028,133, filed on May 21, 2020.

(51) Int. Cl.
*A61L 2/08*    (2006.01)
*A61M 5/00*   (2006.01)

(52) U.S. Cl.
CPC ............... *A61L 2/08* (2013.01); *A61M 5/002* (2013.01)

(58) Field of Classification Search
CPC .................................. A61L 2/08; A61M 5/002
See application file for complete search history.

(56) References Cited

U.S. PATENT DOCUMENTS

| | | | |
|---|---|---|---|
| 9,980,507 B2 * | 5/2018 | Vurma | A23L 29/272 |
| 2004/0043453 A1 * | 3/2004 | Drocourt | G01N 33/569 |
| | | | 435/69.1 |
| 2004/0110841 A1 * | 6/2004 | Kite | A61P 17/00 |
| | | | 514/566 |
| 2012/0114524 A1 | 5/2012 | Sigg | |

(Continued)

FOREIGN PATENT DOCUMENTS

WO    2019042801 A1    3/2019

OTHER PUBLICATIONS

International Search Report issued in PCT/US2021/033657 dated Sep. 16, 2021, 2 pages.

*Primary Examiner* — Jacob K Ackun
(74) *Attorney, Agent, or Firm* — Rothwell, Figg, Ernst & Manbeck, P.C.

(57) ABSTRACT

The present disclosure provides novel processes for providing sterile, pre-filled syringes or injection devices for pharmaceutical compositions, including protein and biopharmaceutical formulations. In some examples, secondary packaging is performed in an aseptic environment, which removes the need for any terminal sterilization method. In some examples, the aseptic packaging method results in a sterile injection device suitable for use in ophthalmic injections.

28 Claims, 4 Drawing Sheets

(56) References Cited

U.S. PATENT DOCUMENTS

| | | |
|---|---|---|
| 2014/0308239 A1* | 10/2014 | Zarbis-Papastoitsis .................. A61P 27/04 514/769 |
| 2016/0279139 A1 | 9/2016 | Shah et al. |
| 2018/0153942 A1 | 6/2018 | Giacalone et al. |
| 2018/0325728 A1 | 11/2018 | Weikart et al. |
| 2019/0365565 A1 | 12/2019 | Bryant et al. |

* cited by examiner

SYSTEMS AND METHODS FOR PRODUCING STERILE INJECTION DEVICES

This application is a 35 U.S.C. 371 National Phase Entry Application from PCT/US2021/033657 filed May 21, 2021, which claims priority to and the benefit of U.S. Provisional Patent Application No. 63/028,133, filed on May 21, 2020, the disclosures of which are incorporated herein by reference in their entirety.

FIELD OF THE INVENTION

The subject matter disclosed herein relates to systems and methods for producing sterile injection devices, including pre-filled syringes for ophthalmic use.

BACKGROUND OF THE INVENTION

Aqueous drug products, including the therapeutic drug substance in the drug product, are subjected to mechanical and chemical stresses when they are manufactured, packaged, transported, stored, and handled prior to administration to a patient. These stresses are detrimental to all drug substances including biologic drug substances (e.g. protein drugs) and non-biologic drug substances (e.g. small molecule drugs). Drug substances are known to degrade or fragment when subjected to mechanical stresses such as physical impact and shear stress. Drug substance, and inactive components of drug products, can also be degraded by unwanted chemical modifications such as oxidation or alkylation. Additionally, proteins are known to aggregate when subject to such stresses. This is a problem because aggregated and degraded drugs have a reduced therapeutic benefit to patients and in some cases may be immunogenic.

Many therapeutic ophthalmic compositions are delivered by intraocular injection (injection into the eye). These drugs may be presented in glass vials from which the drug is drawn with a syringe shortly before injection into the eye. Alternatively, ophthalmic pharmaceutical compositions are often delivered in small dosages in pre-filled syringes. Pre-filled syringes have many benefits compared to a vial and a separately provided syringe, such as improved convenience, affordability, accuracy, sterility, and safety. The use of pre-filled syringes results in greater dose precision, in a reduction of the potential for needle sticks injuries that can occur while drawing medication from vials, in premeasured dosage reducing dosing errors due to the need to reconstitute and/or draw medication into a syringe, and in less overfilling of the syringe helping to reduce costs by minimizing drug waste.

It is important for patient safety and integrity of syringe contents that a syringe be sterile to avoid infection or other risks. Pre-filled syringes with ophthalmic pharmaceutical compositions are regulated as ophthalmic dispensers. Per the United States Food and Drug Administration's ("FDA's") Code of Federal Regulations Title 21, Section 200.50, these ophthalmic dispensers are required to be "packaged so as to maintain sterility until the package is opened." Secondary packaging steps for non-ophthalmic, prefilled syringes are typically performed in non-aseptic environments, in part because the majority of prefilled syringe products only require the sterility of the drug inside of the syringe. This is in contrast to ophthalmic prefilled syringes, which additionally require the sterility of the external surface of the syringe.

Sterilizing the composition and the pre-filled syringe or other injection device presents a number of technical and safety challenges. For example, the ophthalmic pharmaceutical composition is typically sterilized, and then filled into a syringe in one location, and the filled syringe is then securely packaged and terminally sterilized in another location. The movement between locations requires several sterilization steps.

For small volume syringes, for example those for injections into the eye in which it is intended that about 0.1 ml or less of liquid is to be injected, the sterilization can pose difficulties that are not necessarily associated with larger syringes. Changes in pressure, internal or external to the syringe, can cause parts of the syringe to move unpredictably, which may alter sealing characteristics and potentially compromise sterility. Incorrect handling of the syringe can also pose risks to product sterility.

Furthermore, certain therapeutics such as biologic molecules are particularly sensitive to sterilization, be it gas sterilization, thermal sterilization, irradiation, or other sterilization methods discussed herein. Changes in pressure, which may occur for instance after heating, may cause air bubbles contained in the syringe to extend and parts of the syringe to move. This can affect the tightness of the seals on the syringe and may compromise sterility of the prefilled syringe. The tightness of the pre-filled syringe is not only relevant for maintaining the sterility of the syringe and its content, but it also protects the contents of the syringe from the sterilizing gas. If the pre-filled syringe is not appropriately sealed, significant amounts of the gas may intrude into the volume chamber of the syringe and have a detrimental effect on the drug. Further, introduction of such residuals can also have toxicity effects. Ethylene oxide, for instance, alkylates proteins and may therefore alter or inactivate therapeutic proteins. Thus, a careful balancing act is required to ensure that while a suitable level of sterilization is carried out, the syringe remains suitably sealed, such that the therapeutic is not compromised. Of course, the syringe must also remain easy to use, in that the force required to depress the plunger to administer the medicament must not be too high.

To achieve sterility within the secondary packaging of the prefilled syringe, a terminal sterilization method, such as ethylene oxide gas, is typically used. However, this method can have limitations in its use for sensitive drug products, such as biologics. Sterilization via ethylene oxide requires placing the drug product in a heated and humidified chamber. Heat and humidity can lead to product instability for biologic drug products. Such instability can cause protein aggregation, fragmentation, and/or inactivation, which can lead to reduced and unpredictable administered dosage amounts, immunogenicity, and harm to the patient. Additionally, ethylene oxide can permeate through the various components of pre-filled syringes, including rubber in a tip cap of the pre-filled syringe or a syringe barrel, e.g., when the syringe barrel comprises a polymer material). Introduction of the ethylene oxide into the syringe barrel can have the toxicity effects or can comprise the therapeutic proteins, as described previously. Further, such existing processes may lead to loss of costly therapeutic. Although other methods for terminal sterilization are possible, such as electron beam, X-ray, and gamma irradiation, these methods can also result in product instability due to their use of radiation. Therefore, special consideration and development is required to develop a terminal sterilization method suitable for biologic drug products, and there are likely products that are too sensitive for any terminal sterilization method. Terminal sterilization of syringes can be problematic and difficult. The seal in syringes is prone to leaking and thus the sterilizing agent may leach into the syringe. For biologic products, this is critical as it is well known that they are particularly sensitive to terminal sterilizing agents such as hydrogen peroxide, which can oxidize the protein, and heat, which can denature the protein.

Ethylene oxide ("ETO") is a colorless gas that is flammable and explosive. The four essential parameters (operational ranges) are: gas concentration (450 to 1200 mg/1); temperature (37 to 63° C.); relative humidity (40 to 80%) (water molecules carry ETO to reactive sites); and exposure time (1 to 6 hours). These influence the effectiveness of ETO sterilization. ETO use is under increased scrutiny, with facilities in the United States being shut down due to environmental and health concerns. Despite these challenges, a process for aseptic secondary packaging of pre-filled syringes or injection devices containing ophthalmic pharmaceutical compositions that avoids the need for terminal sterilization using ETO, radiation, or other methods does not yet exist.

Accordingly, there are needs for syringes and other injection devices and methods of providing them which solve the aforementioned and other problems.

SUMMARY OF THE INVENTION

In accordance with one aspect of the invention a method is provided for providing an aseptically-packaged sterile, injection device containing a pharmaceutical formulation. In certain aspects, the injection device may be a syringe, an ophthalmic syringe, a disposable syringe, a pre-filled injector pen, a cartridge, or an auto-injector device. In certain aspects, the method includes introducing a sterile injection device body, a sterile plunger, and a sterile plunger rod into an aseptic environment. In certain aspects, the method includes sterilizing an ophthalmic pharmaceutical composition. In certain aspects, the pharmaceutical composition is pre-sterilized and introduced into the aseptic environment as a sterile pharmaceutical composition. In certain aspects, the method includes filling the sterile injection device body with the sterilized or sterile ophthalmic pharmaceutical composition in the aseptic environment to produce a sterile filled injection device body. In certain aspects, the method includes stoppering the sterile filled injection device body with the sterile plunger and the sterile plunger rod in the aseptic environment to form a sterile stoppered pre-filled injection device. In certain aspects, the method includes packaging and sealing the sterile stoppered pre-filled injection device into packaging in the aseptic environment to produce the aseptically packaged sterile pre-filled injection device. In certain aspects, the packaging may be a blister pack, a pouch, or other packaging that maintains sterility of the injection device and its contents. In certain aspects, the method avoids the need for a terminal sterilization step, including avoiding the need for ETO sterilization, electron beam, X-ray and gamma irradiation, and other terminal sterilization of the packaged pre-filled injection device product.

In accordance with another exemplary aspect of the invention, the present disclosure provides another method of providing a packaged, pre-filled syringe or injection device. In certain aspects, the method includes sterilizing an ophthalmic pharmaceutical composition. In certain aspects, the method includes filling the sterilized ophthalmic pharmaceutical composition into a sterile syringe body to produce a filled syringe body. In certain aspects, the syringe (or other injection device) body may be silicone free. In certain aspects, the method includes stoppering the filled syringe body with a sterile plunger and a sterile plunger rod to form a sterile stoppered filled syringe body. In certain aspects, the plunger is silicone-free. In certain aspects, the plunger is siliconized. In certain aspects, the method includes packaging and sealing the pre-filled syringe into packaging, including but not limited to blister packaging or a pouch, to produce the packaged, pre-filled syringe. In certain aspects, the packaging and sealing is conducted under aseptic conditions to prepare a sterile pre-filled syringe without the need for terminal sterilization.

In accordance with another exemplary aspect of the invention, the present disclosure provides another method of providing a packaged pre-filled syringe. In certain aspects, the method includes sterilizing an ophthalmic pharmaceutical composition. In certain aspects, the method includes filling a sterile syringe body with the ophthalmic pharmaceutical composition to produce a filled syringe body. In certain aspects, the method includes stoppering the filled syringe body with the sterile plunger and the sterile plunger rod to produce a sterile stoppered pre-filled syringe. In certain aspects, the method includes packaging and sealing the pre-filled syringe into packaging to produce the packaged, pre-filled syringe. In certain aspects, the packaged, pre-filled syringe is configured to receive a sterile needle or sterile cannula to the stoppered pre-filled syringe.

The above and other various aspects are described below with reference to the accompanying drawings.

BRIEF DESCRIPTION OF THE DRAWINGS

The accompanying drawings, which are incorporated herein and form part of the disclosure, help illustrate various exemplary aspects of the present disclosure and, together with the description, further serve to describe exemplary aspects of the invention to enable a person skilled in the pertinent art to make and use the aspects disclosed herein. In the drawings, like reference numbers indicate identical or functionally similar elements.

DETAILED DESCRIPTION

While aspects of the subject matter of the present disclosure may be embodied in a variety of forms, the following description is merely intended to disclose some of these forms as specific examples of the subject matter encompassed by the present disclosure. Accordingly, the subject matter of this disclosure is not intended to be limited to the forms or aspects so described.

Unless defined otherwise herein, all technical and scientific terms used herein have the same meaning as commonly understood by one of ordinary skill in the art.

As used herein the term "aqueous drug substance solution" refers to a liquid or semi-solid that contains water and a drug product and optionally one or more pharmaceutically acceptable excipients.

As used herein, the term "aseptic environment" refers to a facility designed to prevent microbiological contamination. The aseptic environment has, inter alia, floors, walls, and ceilings of smooth, hard surfaces; temperature and humidity controls; an air supply filtered through high-efficiency particulate air filters under positive pressure, regardless of whether flow is laminar or nonlaminar; a system for monitoring environmental conditions; a system for cleaning and disinfecting the room and equipment to produce aseptic conditions; and a system for maintaining any equipment used to control the aseptic conditions.

As used herein the term "biologic drug substance" includes, but is not limited to, vaccines, blood and blood components, allergenics, somatic cells, gene therapy, tissues, isolated natural proteins, recombinant proteins, biogenerics and biosimilars.

The term "biosimilar" or "biosimilars," as used herein, refers to a biological product designed to have active properties similar to an FDA-licensed biological product.

As used herein, the term "colony forming unit" or "CFU" refers to formation of a single macroscopic colony after the introduction of one or more micro-organisms to microbiological growth media.

As used herein, the term "delivery device" refers to a device suitable for delivering a liquid or semi-solid drug product to a patient. The delivery device may be suitable for delivery of drug product directly to a patient or via an intermediary step (e.g. intravenous bag or line). Delivery devices include, for example, screw-on ports, hollow needles, microneedles, cannulas, and jet injectors.

As used herein, the term "injection device" refers to a device suitable for injecting a pharmaceutical composition into ocular tissue of a subject. Injection devices including, for example, a syringe, a disposable syringe, a pre-filled injector pen, a cartridge, and an auto-injector device.

The term "drug product" refers to the active pharmaceutical ingredient in a pharmaceutical product (e.g. an aqueous drug substance solution). In one embodiment, the drug product is a biologic drug substance. In another embodiment, the drug product is a non-biologic drug substance.

As used herein, the term "filling" refers to transferring the aqueous drug substance solution from a bulk container to a container. Containers can be filled individually or a plurality of containers can be filled simultaneously and/or sequentially. Preferably filling occurs in a gaseous environment consisting essentially of ambient atmosphere or at least on soluble gas, more preferably the gaseous environment is at an ambient pressure of about 1 atmosphere. In one embodiment, filling occurs at a temperature at about room temperature. In another embodiment, filling occurs at a temperature from about 15° C. to about 90° C. In another embodiment, filling occurs at a temperature that does not exceed about 90° C., about 85° C., about 80° C., about 75° C., about 70° C., about 65° C., about 60° C., about 55° C., about 50° C., about 45° C., about 40° C., about 35° C., about 30° C., about 25° C., about 20° C., or about 15° C.

The term "filling time" refers to the time used to fill a bulk product into containers until the container is closed.

The term "pharmaceutically acceptable" describes a material that is not biologically or otherwise undesirable (i.e. without causing an unacceptable level of undesirable biological effects or interacting in a deleterious manner).

As used herein the term "protein" refers to a chain of amino acids bound by peptide bonds. Both naturally-occurring proteins, non-naturally-occurring proteins and other polypeptides are included in the present invention. In one embodiment, a protein for use in the present invention is an immunoglobulin. Non-limiting examples of proteins are described herein and additional examples of proteins are known in the art.

As used herein, the term "soluble gas" refers to any gas which dissolves into an aqueous solution. A soluble gas has a greater capacity to dissolve into an aqueous solution than atmosphere. A soluble gas used in the present invention may be a non-reactive gas or an inert gas. Suitable soluble gases include, but are not limited to: carbon dioxide, gaseous water, gaseous ethanol and gaseous formic acid. In one embodiment, the inert gas is carbon dioxide.

The term "sterility assurance level" or "SAL" refers to the probability of microorganisms surviving in a product after exposure to the process. An SAL of $10'$, for example, denotes a probability of not more than 1 non-sterile item in $1\times10^6$ sterilized items of the final product.

As used herein the term "syringe" refers to a chamber attached to a hollow needle or means for attaching a hollow needle wherein the chamber is of sufficient size to house a liquid or semi-solid drug product. As used herein the "closed end" of the syringe refers to the end of the chamber having the attached hollow needle or means for attaching the hollow needle. As used herein the term "open end" of the syringe refers to the end of the chamber opposite the closed end. The "open end" of the syringe is configured as to receive a liquid or semi-solid drug product. The "proximal end" of the open end of the syringe refers to the end closest to the closed end of the syringe. The "distal end" of the open end of the syringe refers to the end farthest from the closed end of the syringe.

As used herein, the term "stopper" refers to any article capable of preventing the aqueous drug substance solution from exiting the open end of the container.

Stability of a drug substance in an aqueous solution may also be defined as the percentage of monomer, aggregate, or fragment, or combinations thereof, of the protein in the formulation. A drug substance "retains its physical stability" in a solution if it shows substantially no signs of aggregation, precipitation and/or denaturation upon visual examination of color and/or clarity, or as measured by UV light scattering or by size exclusion chromatography. In one embodiment of the invention, a stable aqueous solution is a solution having less than about 10%, 9%, 8%, 7%, 6%, 5%, 4%, 3%, 2%, 1%, 0.5%, 0.3%, 0.2%, or 0.1% of the protein being present as aggregate in the solution.

As used herein, the term "substantially free" means that either no substance is present or only minimal, trace amounts of the substance are present which do not have any substantial impact on the properties of the composition. In a particular embodiment, a composition is substantially free of a substance if at least 95%, 96%, 97%, 98%, 99%, 99.5%, or 99.8% of the substance has been removed. In another embodiment, substantially free means the substance is not present in amount sufficient to perform a function in composition for which a skilled artisan would use the substance. If reference is made to no amount of a substance, or a composition being free of a substance, it should be understood as "no detectable amount."

The singular forms "a," "an," and "the" include plural referents unless the context clearly dictates otherwise.

The term "treating" or "treatment" as used herein and as is well understood in the art, means an approach for obtaining beneficial or desired results, including clinical results. Beneficial or desired clinical results can include, but are not limited to, alleviation or amelioration of one or more symptoms or conditions, diminishment of extent of disease, stabilizing (i.e. not worsening) the state of disease, delaying or slowing of disease progression, amelioration or palliation of the disease state, diminishment of the reoccurrence of disease, and remission (whether partial or total), whether detectable or undetectable. "Treating" and "treatment" can also mean prolonging survival as compared to expected survival if not receiving treatment. In addition to being useful as methods of treatment, the methods described herein may be useful for the prevention or prophylaxis of disease.

The phrase "terminal sterilization" and grammatical variations thereof refer to an assembled product, typically already in its associated packaging, that is sterilized using heat, radiation, and/or chemically, e.g., using a sterilizing gas. Such a process may involving using an ethylene oxide (ETO) or a hydrogen peroxide ($H_2O_2$) sterilization process. Needles to be used with the syringe may be sterilized by the same method, as may kits according to some aspects of the present disclosure. In some aspects of the present disclosure, terminal sterilization is not used. In a terminal sterilization process, a syringe, product, kit, needle, or package may be exposed to the sterilizing gas until the outside of the syringe, product, kit, needle, or package is sterile.

Nitrogen dioxide ($NO_2$) sterilization is another chemical-based sterilization method. The active sterilant is the gas phase of $NO_2$, which exists above 21.2° C. The gas phase of $NO_2$ can readily penetrate device packaging and sterilize medical devices by creating single strand breaks in DNA. This sterilization process is validated using the overkill method (similarly to ETO) to achieve a sterility assurance level of 10'. The residues present after sterilization are nitrogen-based and are at relatively low levels because of the sterilization mechanism. $NO_2$ is compatible with many materials except for polyurethane, nylon, polyacetal, copper (and alloys), nitinol, and cellulose-based materials.

Chlorine Dioxide ($ClO_2$) sterilization is a chemical-based sterilization method. The active sterilant is the gas phase of $ClO_2$. The gas phase of $ClO_2$ can readily penetrate device packaging and sterilize medical devices through an oxidative mechanism at low sterilant concentration at room temperature and at atmospheric pressure. This sterilization process is validated using the overkill method to achieve a sterility assurance level of $10^{-6}$. The residues formed during this sterilization process are chlorine dioxide, chlorates, and chlorite that have low toxicity concerns from the reported literature. Although material compatibility information is limited, $ClO_2$ is not known to be incompatible with the most commonly used materials in medical devices such as stainless steel and some polymers.

Vaporized Peracetic Acid ($CH_3CO_3H$) sterilization is a chemical-based sterilization method. The active sterilant is the reactive molecules found in the vapor phase between acetic acid and peracetic acid. The reactive molecules found in the vapor phase readily penetrate device packaging and sterilize medical devices through an oxidative mechanism that denatures proteins, disrupts cell wall permeability, and oxidizes sulfhydryl and disulfide bonds in proteins, enzymes, and other metabolites at low temperatures. This sterilization process is validated using the overkill method to achieve a sterility assurance level of $10^{-6}$. The residues formed during this sterilization process are acetic acid, peracetic acid, water, and oxygen, which have low toxicity concerns. $CH_3CO_3H$ is known to be compatible with a wide range of materials used in the construction of medical devices such as stainless steel and many polymers.

In one aspect, the pre-filled syringe may have a Sterility Assurance Level of $10^{-6}$ or better. That is, the probability that a single spore that has been subjected to sterilization nevertheless remains nonsterile is one in a million.

In one aspect, significant amounts of the sterilizing gas has not entered the variable volume chamber of the syringe. The term "significant amounts" as used herein refers to an amount of gas that would cause unacceptable modification of the ophthalmic solution within the variable volume chamber. In one embodiment, the sterilization process does not cause alkylation of the biologic drug, e.g., a VEGF antagonist.

In certain aspects, the pre-filled syringe has been sterilized using ETO, but the outer surface of the syringe has ≤1 ppm, preferably ≤0.2 ppm ETO residue. In certain aspects, the pre-filled syringe has been sterilized using hydrogen peroxide, but the outer surface of the syringe has ≤1 ppm, preferably ≤0.2 ppm hydrogen peroxide residue. In certain aspects, the pre-filled syringe has been sterilized using ETO, and the total ETO residue found on the outside of the syringe and inside of the packaging is ≤0.1 mg. In certain aspects, the pre-filled syringe has been sterilized using hydrogen peroxide, and the total hydrogen peroxide residue found on the outside of the syringe and inside of the packaging is ≤0.1 mg. In certain aspects, the packaging is a blister pack or a pouch.

In certain aspects, the outer surface of the syringe, product, kit, needle, or package may remain sterile (e.g., whilst in a blister pack or other packaging) for up to 6 months, 9 months, 12 months, 15 months, 18 months, 24 months or longer. Thus, in one embodiment, a syringe, product, kit, needle, or package according to the present disclosure (e.g., whilst in a blister pack or other packaging) may have a shelf life of up to 6 months, 9 months, 12 months, 15 months, 18 months, 24 months or longer. In one embodiment, less than one syringe or needle in a million has detectable microbial presence on the outside of the syringe or needle after 18 months of storage.

Concentrations, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 0.01 to 2.0" should be interpreted to include not only the explicitly recited values of about 0.01 to about 2.0, but also include individual values and sub-ranges within the indicated range. Thus, included in this numerical range are individual values such as 0.5, 0.7, and 1.5, and sub-ranges such as from 0.5 to 1.7, 0.7 to 1.5, and from 1.0 to 1.5, etc.

In understanding the scope of the present disclosure, the terms "including" or "comprising" and their derivatives, as used herein, are intended to be open ended terms that specify the presence of the stated features, elements, components, groups, integers, and/or steps, but do not exclude the presence of other unstated features, elements, components, groups, integers and/or steps. The foregoing also applies to words having similar meanings such as the terms "including", "having" and their derivatives. The term "consisting" and its derivatives, as used herein, are intended to be closed terms that specify the presence of the stated features, elements, components, groups, integers, and/or steps, but exclude the presence of other unstated features, elements, components, groups, integers and/or steps. The term "consisting essentially of", as used herein, is intended to specify the presence of the stated features, elements, components, groups, integers, and/or steps as well as those that do not materially affect the basic and novel characteristic(s) of features, elements, components, groups, integers, and/or steps. It is understood that reference to any one of these transition terms (i.e. "comprising," "consisting," or "consisting essentially") provides direct support for replacement to any of the other transition term not specifically used. For example, amending a term from "comprising" to "consisting essentially of" would find direct support due to this definition.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the associated description herein. For example, in one aspect, the degree of flexibility can be within about ±10% of the numerical value. In another aspect, the degree of flexibility can be within about ±5% of the numerical value. In a further aspect, the degree of flexibility can be within about ±2%, ±1%, or ±0.05%, of the numerical value.

Generally, herein, the term "or" includes "and/or."

As used herein, a plurality of compounds or steps may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

In any of the aspects of the invention, the aqueous drug substance solution may comprise a biologic or non-biologic drug substance. The non-biologic molecule solution may be a pharmaceutical composition comprising a small molecule. The biologic drug substance may be a protein. The biologic drug substance may also be an antibody, fusion protein, polypeptide, or conjugated protein.

In any of the embodiments of the invention, the aqueous drug substance solution may be stable for at least one week at 40° C. or two weeks at 25° C.

In any of the aspects of the present disclosure, the aqueous drug substance solution may be stable (i) for at least three months; (ii) for at least six months; or (iii) for at least one year.

In any of the aspects of the present disclosure, the aqueous drug substance solution may have stability comparable to, or better than, the same aqueous drug substance solution in a container made according to conventional methods.

In one aspect, the aqueous drug substance solution has fewer subvisible particles than an aqueous solution of the same drug substance that contains surfactant in a container made according to conventional methods.

In any of the aspects of the invention, process steps may be performed within specifically defined areas of adequate size. Separate or defined areas or such other control systems for processes as are necessary to prevent contamination or mix-ups during the course of the following procedures are provided:

(1) Receipt, identification, storage, and withholding from use of components, drug product containers, closures, and labeling, pending the appropriate sampling, testing, or examination by the quality control unit before release for manufacturing or packaging;
(2) Holding rejected components, drug product containers, closures, and labeling before disposition;
(3) Storage of released components, drug product containers, closures, and labeling;
(4) Storage of in-process materials;
(5) Manufacturing and processing operations;
(6) Packaging and labeling operations;
(7) Quarantine storage before release of drug products;
(8) Storage of drug products after release;
(9) Control and laboratory operations;
(10) Aseptic processing, which includes as appropriate:
(i) Floors, walls, and ceilings of smooth, hard surfaces that are easily cleanable;
(ii) Temperature and humidity controls;
(iii) An air supply filtered through high-efficiency particulate air filters under positive pressure, regardless of whether flow is laminar or nonlaminar;
(iv) A system for monitoring environmental conditions;
(v) A system for cleaning and disinfecting the room and equipment to produce aseptic conditions; and
(vi) A system for maintaining any equipment used to control the aseptic conditions.

The present disclosure provides novel processes for providing sterile, pre-filled syringes of pharmaceutical compositions. In some examples, secondary packaging is performed in an aseptic environment, which removes the need for any terminal sterilization steps or processes. The disclosed processes mitigate typical concerns with product quality by ensuring sterility of the syringes while simultaneously providing commercial-scale manufacturing capability and practical usability, even when the syringes are used in delicate and precise medical procedures. The disclosed processes further reduce environmental impact of providing pre-filled syringes by reducing the harmful compounds and hazardous procedures needed to produce each syringe and the number of locations involved in the production. Additionally, the disclosed processes also reduce costs and simplify the process of sterilization, to provide processes which are simpler from a supply chain perspective and can take place continuously within a single site. Altogether, the disclosed processes reduce time and complexity by removing shipping, batch release, and processing steps, as required by conventional processes, while also avoiding environmental and health hazards.

Figure 1A:
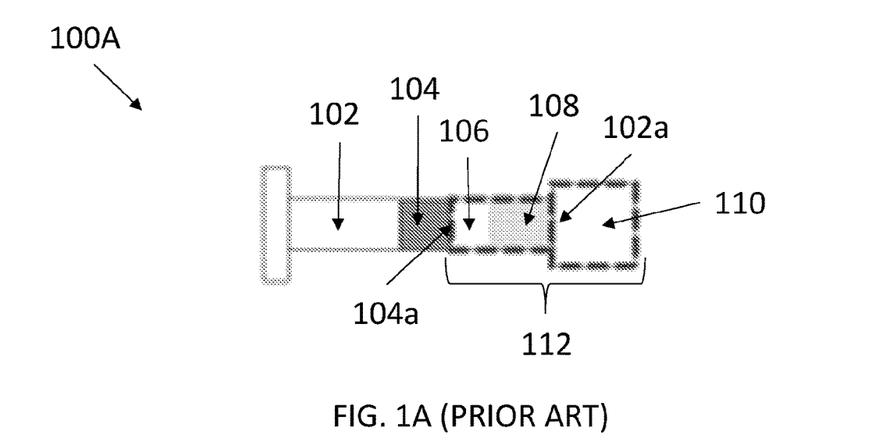
FIG. 1A shows an exemplary stoppered filled syringe, according to the prior art.
Figure 1B:
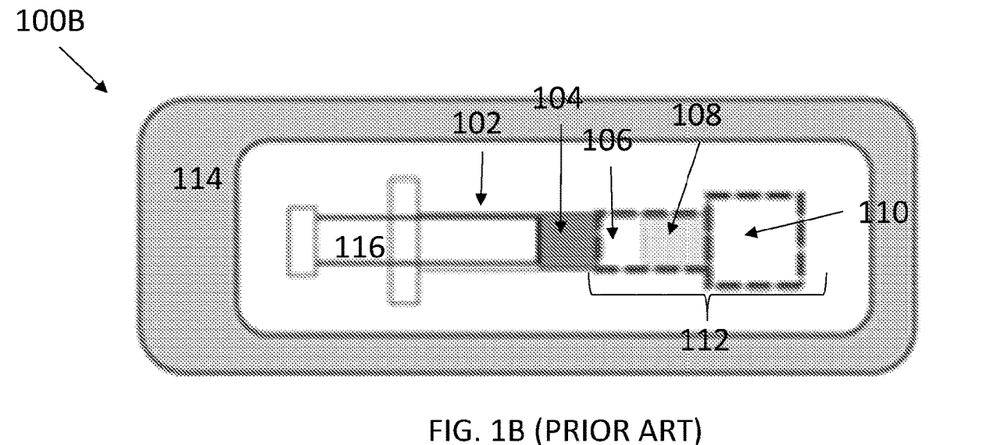
FIG. 1B shows an exemplary packaged, pre-filled syringe, according to the prior art.
Figure 1C:
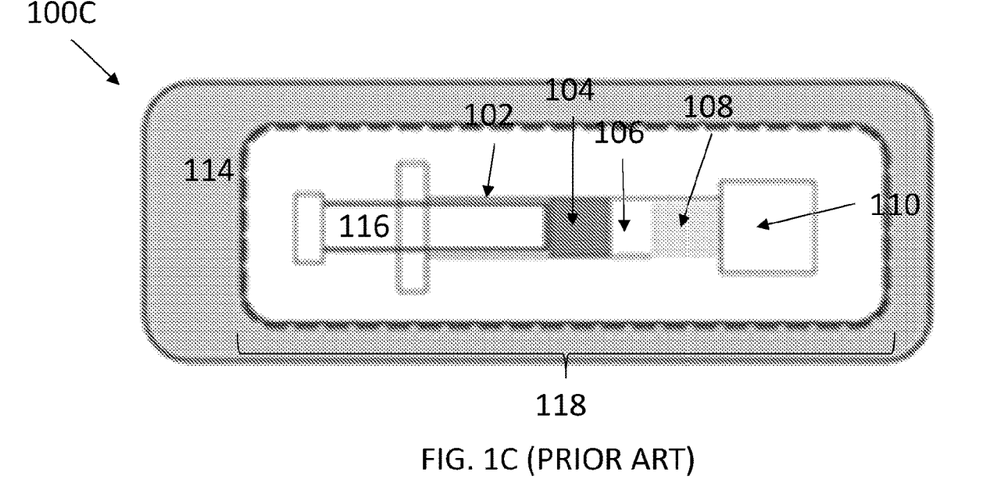
FIG. 1C shows an exemplary sterilized, packaged, pre-filled syringe according to the prior art.

FIGS. 1A-1C show exemplary steps during a standard terminal sterilization process for an ophthalmic pre-filled syringe, according to the prior art.

Turning first to FIG. 1A, a stoppered, filled syringe 100A is shown during an exemplary first step of a conventional process for providing pre-filled syringes. Syringe 100A includes a syringe body 102, a plunger 104, an air bubble 106, an ophthalmic pharmaceutical composition 108, an optional cap 110, and a sterilization barrier 112.

To produce the syringe 100A, a sterile syringe body 102 and sterile plunger 104 are introduced into a first environment as a first step of a multi-step process for producing the syringe 100A. For example, the first environment is aseptic.

In some examples, a cap 110 is pre-sterilized and is introduced into the first environment with the sterile syringe body 102 and the sterile plunger 104. The cap 110 is then affixed to the first end 102a of the syringe 102 to seal the syringe 102 at the first end 102a before the syringe is filled.

In other examples, the cap 110 is assembled onto the syringe body 102 outside of the first environment. For example, multiple syringe bodies 102, which are assembled with caps 110, are put into a suitable container, the container is sealed and terminally sterilized, and then the terminally sterilized container is introduced into the first environment. The terminal sterilization may be performed by ethylene oxide gas, electron beam or gamma irradiation, or other terminal sterilization methods as used in the art.

Within the first environment, an ophthalmic pharmaceutical composition 108 is then sterilized. For example, the ophthalmic pharmaceutical composition 108 is sterilized with an in-line filter (not shown), provided separately in the first environment.

In some examples, the ophthalmic pharmaceutical composition 108 is pre-sterilized before introduction into the first environment. For example, the ophthalmic pharmaceutical composition 108 is pre-sterilized with a filter into a sterile bag, and the sterile bag is introduced into the first environment.

The ophthalmic pharmaceutical composition 108 is then filled into the syringe 102 in the first environment. In examples where the sterile bag with the pre-sterilized ophthalmic pharmaceutical composition 108 is introduced into the first environment, the sterile bag is connected directly to a filling system and filled into the syringe 102 without an in-line filter.

The syringe 102 is then stoppered with the plunger 104 in the first environment to preserve the sterility of the ophthalmic pharmaceutical composition. An air bubble 106 may be provided in the syringe 102 between a first end 102a of the syringe 102 and the stopper 104.

Therefore, this first step of a conventional sterilization process provides a sterility barrier 112 around the cap 110, the ophthalmic pharmaceutical composition 108, the air bubble 106, and a proximal surface 104a of the plunger 104. This sterility barrier 112 relies on integrity of a seal between an outer circumferential surface of the plunger 104 and an inner circumferential surface of the syringe body 102. After the syringe 100A leaves the first environment, unsealed/exposed areas of the syringe 100A are no longer considered to be sterile. Therefore, after departure from the first environment, all parts of the syringe 100A that are not encompassed by the sterility barrier 112 are considered contaminated and must be re-sterilized before use of the syringe 100A with a patient.

In the second step of conventional processes for providing pre-filled syringes, syringe 100A is shipped to a second environment for assembly and packaging steps. This second environment is non-aseptic. Therefore, the sterility barrier 112 remains unchanged.

FIG. 1B shows an exemplary packaged, pre-filled syringe 100B, during an exemplary second step of a conventional process for providing pre-filled syringes. Syringe 100B includes similar labels and elements as syringe 100A of FIG. 1A. Syringe 100B further includes packaging 114 and a plunger rod 116. During an assembly step, a plunger rod 116 is inserted into the syringe body 102 to abut the plunger 104. The assembled syringe is then placed into packaging 114.

In the third step of conventional processes for providing pre-filled syringes, the packaged, pre-filled syringe 100B is shipped to a third environment for performing a terminal sterilization process. This terminal sterilization process reduces any bacteria and spores in the packaged, pre-filled syringe 100B and is legally required before the syringe 100B is provided to a user.

FIG. 1C shows an exemplary sterilized, packaged, pre-filled syringe 100C during an exemplary third step of a conventional process for providing pre-filled syringes. Syringe 100C includes similar labels and elements as syringes 100A and 100B of FIGS. 1A and 1B, respectively. Syringe 100C further includes a second sterility barrier 118. At the third environment, the syringe 100C is terminally-sterilized, while sealed in packaging 114. For example, the terminal sterilization is performed by ethylene oxide gas, electron beam or gamma irradiation, or other terminal sterilization methods as used in the art. Therefore, the sterility of syringe 100C is assured through seal integrity of the packaging 114.

Altogether, FIGS. 1A-1C show the tedious, step- and location-intensive processes that are conventionally used to provide sterilized syringes. As discussed herein, the present disclosure provides novel processes and novel syringes, which maintain sterility while streamlining the steps required to provide a sterile syringe to a patient.

Figure 2:
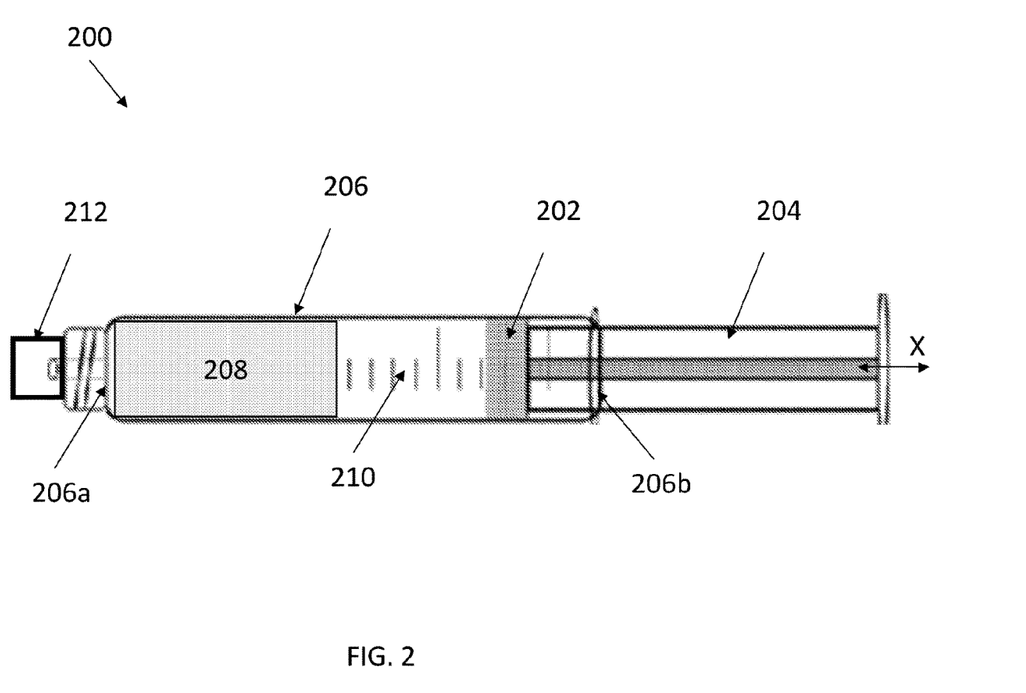
FIG. 2 shows an exemplary syringe, according to the various embodiments of the present disclosure.

FIG. 2 shows an exemplary syringe 200, according to the various embodiments of the present disclosure. Syringe 200 includes a plunger 202, a plunger rod 204, a syringe body 206, a pharmaceutical composition 208, an optional air bubble 210, and an optional cap 212. In some examples, syringe 200 is an injection device, cartridge, or dispenser.

The syringe body 206 includes a barrel made of an inert gas-impermeable material for retaining one or more types of fluids. In one aspect, the syringe body 206 has a circular circumference. In other aspects, the syringe body 206 has a non-circular, polygonal shape. The syringe body 206 is hollow to receive the pharmaceutical composition 208, the plunger 202, and the plunger rod 204. In some examples, an interior circumferential portion of the syringe body 206 is coated with a hydrophilic composition or is subject to a hydrophilic treatment. In some examples, the interior circumferential portion of the syringe body 206 is coated with silicone oil or another lubricating agent.

Silicone oil may be used as a lubricant as the plunger 202 moves along the barrel of the syringe body 206. Ease of movement during an injection is very important. For example, unexpected perturbations can cause the syringe to move in the eyeball of a patient during an injection. Examples of perturbations include an irregular injection due to stopping friction of the plunger 202 along the syringe body 206, viscous drag of the pharmaceutical composition 208, and fluid inertia of the pharmaceutical composition 208. These unintended movements cause damage to the eye, and can cause the injection to go into an undesired region of the eye.

Protein aggregates, misfolded proteins, and/or fragments may cause immunogenic reactions, typically involving the formation of neutralizing antibodies that decrease physiologically effective concentration of the therapeutic drug and triggering severe allergic responses like anaphylaxis or serum sickness. A well reported example of a severe immunogenic reaction is the pure red cell aplasia, resulting from the formation of anti-erythropoietin antibodies. Such undesired proteinaceous particles in a composition may also cause an immune response via T cell wherein T cells recognize repetitive patterns on the surface of aggregates which are similar to the unique epitope arrangement of microbial antigens. Factors like temperature, pH, shaking, shearing are considered to be major reasons for the formation of protein aggregates. Silicone oil used as lubricant in glass syringes, vial and syringe stoppers plus the material of stoppers is also reported to induce protein aggregation/particle formation. In addition, factors like accidental freeze thaw, exposure to light might also contribute to proteinaceous particle generation. The present disclosure includes methods and syringes that minimize such proteinaceous particles and have reduced immunogenicity compared to existing biologic injectable products. The present disclosure provides methods and pre-filled syringes that minimize the particulates which may pose risk of immunogenicity to the human body without undue increase in the gliding or break force. Further, the present disclosure provides methods and pre-filled syringes having little to no protein binding so as to avoid reduction of the administered dose due to binding of the protein drug to the syringe.

The syringe body 206 includes an ejection end 206a and a plunger end 206b. The ejection end 206a is configured with an opening to receive a needle or cannula (not shown). Therefore, the syringe 200 can be configured to release the pharmaceutical composition 208 from the ejection end 206a of the syringe body 206. In some examples, the ejection end 206a of the syringe body 206 is further configured to receive a cap 212. For example, the cap 212 can create an airtight seal of the opening to prevent the pharmaceutical composition 208 from leaking out of the ejection end 206a. For example, the ejection end 206a of the syringe body 206 has an opening (not shown). The plunger end 206b of the syringe body receives the plunger 202 and the plunger rod 204. In some aspects, the syringe body 206 is made of glass, siliconized glass, or plastic. For example, the plastic may be polypropylene, polyethylene, cyclic olefin polymer, cyclic olefin copolymer, or other polymeric material. The syringe body may be coated with a film, e.g., a fluoropolymer film, or a lubricant coating, including but not limited to silicone oil or other lubricating agent such as a perfluoropolyether compound, or may be uncoated.

The plunger 202 is configured to snuggly fit within the barrel of the syringe body 206, as shown in FIG. 2. The plunger 202 is removable from the syringe body 206. For example, the plunger 202 also has a circular circumference. In some examples, the plunger 202 is malleable, or comprises a malleable material along an outer circumferential surface of the plunger 202. In some aspects, the plunger 202 is made of a rubber-containing or a silicone-containing material. In some aspects, the plunger 202 may be siliconized. For example, the rubber may be a butyl rubber, e.g., a bromobutyl rubber or a chlorobutyl rubber. In some examples, the plunger 202 is coated with a silicone oil. In some aspects, the plunger 202 is silicone-free and does not include a silicone oil coating. The front surface of the plunger 202 may be any suitable shape, for example substantially planar, substantially conical or of a domed shape. The rear surface of the plunger 202 may include a substantially central recess. Such a central recess could be used to connect a plunger rod to the plunger 202 using a snap fit feature or thread connection. In some aspects, the plunger 202 is threaded. In some aspects, the plunger 202 is non-threaded. The plunger 202 may be substantially rotationally symmetric about an axis through the plunger 202.

The plunger 202 is configured to form an airtight seal between the outer circumferential surface of the plunger 202 and the inner circumferential surface of the syringe body 206. For example, the plunger 202 seals the pharmaceutical composition 208 in the syringe body 206. In some examples, the plunger 202 further traps an air bubble 210 in the syringe body 206.

In some aspects, the plunger rod 204 is made of a polymer or polymer blend, e.g., polypropylene, polystyrene, polycarbonate, a combination thereof, or similar polymeric material. Movement of the plunger rod 204 along a horizontal axis X moves the plunger 202 along the barrel of the syringe body 206. In some examples, the plunger rod 204 is coupled to the plunger 202. In some examples, the plunger rod 204 and the plunger 202 are a single material.

The pharmaceutical composition 208 can be any liquid and/or gaseous composition, e.g., for medical use. For example, the pharmaceutical composition 208 is an ophthalmic pharmaceutical composition, including a vascular endothelial growth factor (VEGF) antagonist, including any of: antibodies directed against VEGF or VEGFR, soluble VEGFR/VEGFR hybrids, tyrosine kinase inhibitors, steroids, antibiotics, antiviral agents, and antifungal agents. As non-limiting examples, the pharmaceutical composition 208 may contain bevacizumab (commercially sold as Avastin®), ranibizumab (commercially sold as Lucentis®), aflibercept (commercially sold as Eylea®), brolucizumab (commercially sold as Beovu®), pegaptanib (commercially sold as Macugen®), triamcinolone acetonide (commercially sold as Triesence®), anecortave acetate (commercially sold as Retaane®), triamcinolone acetonide (commercially sold as Kenalog®), ganciclovir, foscarnet, cidofovir, fomvirsen, methotrexate, vancomycin, ceftazidime, amikacin, amphotericin B, voriconazole, dexamethasone, or a derivative, analog, generic, or biosimilar version thereof.

The term "VEGF-antagonist" refers to a molecule which specifically interacts with VEGF and inhibits one or more of its biological activities, for example its mitogenic, angiogenic and/or vascular permeability activity. It is intended to include both anti-VEGF antibodies and antigen-binding fragments thereof and non-antibody VEGF-antagonists.

Non-antibody VEGF-antagonists include Aflibercept, Pegaptanib, and antibody mimetics. Aflibercept which is presently marketed under the name Eylea® is a recombinant human soluble VEGF receptor fusion protein in which portions of human VEGF receptors 1 and 2 extracellular domains are fused to the Fc portion of human IgG1 (Holash et al. (2002) Proc. Natl. Acad. Sci. USA 99(17): 11393-11398; WO 00/75319 A1). Pegaptanib which is presently marketed under the name Macugen® is a pegylated anti-vascular endothelial growth factor (VEGF) aptamer (Bell et al. (1999) In Vitro Cell Dev Biol Anim. 35(9): 533-42). Antibody mimetics which are VEGF-antagonists include binding proteins comprising an ankyrin repeat domain that binds VEGF and inhibits its binding to the receptor, such as DARPin® MP0112 (see also WO 2010/060748 and WO 2011/135067).

The term "anti-VEGF antibody" refers to an antibody or antibody fragment such as a Fab or an scFV fragment that specifically binds to VEGF and inhibits one or more of its biological activities, for example its mitogenic, angiogenic and/or vascular permeability activity. Anti-VEGF antibodies act, for example, by interfering with the binding of VEGF to a cellular receptor, by interfering with vascular endothelial cell activation after VEGF binding to a cellular receptor, or by killing cells activated by VEGF. Anti-VEGF antibodies include, for example, antibodies A4.6.1, Bevacizumab, Ranibizumab, G6, B20, 2C3, and others as described in, for example, WO 98/45331, US 2003/0190317, U.S. Pat. Nos. 6,582,959, 6,703,020, WO 98/45332, WO 96/30046, WO 94/10202, WO 2005/044853, EP 0 666 868 B 1, WO 2009/155724 and Popkov et al. (2004) J. Immunol. Meth. 288: 149-64. The anti-VEGF antibody or antigen-binding fragment thereof present in the pharmaceutical composition may be, for example, Ranibizumab or Bevacizumab.

"Ranibizumab" is a humanized monoclonal Fab fragment directed against VEGF-A having the light and heavy chain variable domain sequences of Y0317 as described in SEQ ID Nos. 115 and 116 of WO 98/45331 and Chen et al. (1999) J. Mol. Biol. 293: 865-81. The CAS number of Ranibizumab is 347396-82-1. Ranibizumab inhibits endothelial cell proliferation and neovascularisation and has been approved for the treatment of neovascular (wet) age-related macular degeneration (AMD), the treatment of visual impairment due to diabetic macular oedema (DME), the treatment of visual impairment due to macular oedema secondary to retinal vein occlusion (branch RVO or central RVO), or treatment of visual impairment due to choroidal neovascularisation (CNV) secondary to pathologic myopia. Ranibizumab is related to Bevacizumab and derived from the same parent mouse antibody as Bevacizumab but it is much smaller than the parent molecule and has been affinity matured to provide stronger binding to VEGF-A. Ranibizumab may be produced recombinantly in *Escherichia coli*, for example as described in WO 98/45331 A2. The commercial LUCENTIS® (ranibizumab) formulation contains α,α-trehalose dihydrate, histidine hydrochloride, polysorbate 20 and water for injection and is supplied in a concentration of 10 mg/ml.

"Bevacizumab" is a full-length, humanized murine monoclonal antibody that recognizes all isoforms of VEGF and which is the parent antibody of Ranibizumab. The CAS number of Bevacizumab is 216974-75-3. Bevacizumab inhibits angiogenesis and is presently approved for the treatment of different cancer types.

Aflibercept, marketed under the name Eylea®, is a recombinant fusion protein consisting of the VEGF binding portion from the extracellular domains of human VEGF receptors 1 and 2 that are fused to the Fc portion of the human IgG1 immunoglobulin. It is approved for the treatment of wet macular degeneration. The CAS number of Aflibercept is 862111-32-8. It has received a marketing authorization for the treatment of wet age-related macular degeneration, visual impairment due to diabetic macular oedema (DME) and diabetic retinopathy in patients with diabetic macular edema. [0267] The antibody concentration within the pre-filled syringes of the present invention is typically 1-100 mg/ml, preferably 2-75 mg/ml, more preferably 3-50 mg/ml, even more preferably 5 to 30 mg/ml and most preferably 6 or 10 mg/ml.

The drug contained in the pre-filled syringe of the present invention, i.e. the VEGF-antagonist, preferably an anti-VEGF antibody, is stable at a temperature of 2 to 8° C. (about 35° F. to about 46° F.) for at least six months, preferably for at least 9 months, more preferably for at least one year, particularly preferably for at least 18 months and most preferably for about two years. The drug contained in the pre-filled syringe of the present invention, i.e. the VEGF-antagonist, preferably an anti-VEGF antibody and more preferably Ranibizumab, is stable at room temperature, i.e. a temperature between 15° C. and 25° C., for at least three days or one week, preferably for at least two or three weeks, more preferably for about 4 weeks and most preferably for at least three months. The drug contained in the pre-filled syringe of the present invention, i.e. the VEGF-antagonist, preferably an anti-VEGF antibody or a VEGF receptor fusion protein and more preferably Ranibizumab or Aflibercept, is stable at a temperature of about 40° C. (about 104° F.) for at least four or six hours, preferably for at least 10 or 12 hours, more preferably for at least 18 or 24 hours and most preferably for one or two weeks.

The stability of the drug within the syringe can, for example, be determined by ion exchange chromatography or peptide mapping, by which modifications of the drug such as oxidized and deamidated species can be detected or by size exclusion chromatography, by which aggregates of the drugs can be detected. A description of such an analysis is provided in the examples section.

The drug, i.e. the VEGF-antagonist, preferably the anti-VEGF antibody, is considered stable, if the sum of all impurities comprising aggregates and chemically modified species is less than 2%, preferably less than 1.5%, more preferably less than 1.2% and most preferably less than 1% compared to the amount of non-modified, non-aggregated drug.

In some aspects, the pharmaceutical composition 208 includes an active pharmaceutical ingredient for treating geographic atrophy, also known as atrophic age-related macular degeneration (AMD) or advanced dry AMD. In some aspects, the active pharmaceutical ingredient binds to C3 (non-limiting examples include but are not limited to Apl-2 and NGM621).

In some examples, one or more of the plunger 202, the plunger rod 204, the syringe body 206, and the cap 212 are sterile.

In some examples, syringe 200 is configured to eject the pharmaceutical composition 208 from the syringe body 206 at a rate between 0.01 mL/s and 0.10 mL/s. In some examples, syringe 200 is configured to eject the pharmaceutical composition 208 from the syringe body 206 at a rate of less than 0.06 mL/s, e.g., 0.05 mL/s or 0.04 mL/s.

For example, in some embodiments, syringe 200 may comprise an autoinjector or pen injector. Other details surround the features of autoinjectors and pen injectors, as used for the purposes of the present disclosure, can be found at Goldfarb, Landon, "Pen and Autoinjectors: Testing for the Future" Medical Design Briefs (September 2019) accessed at medicaldesignbriefs.com/component/content/article/mdb/features/articles/35082, the contents of which are incorporated herein in their entireties.

In one aspect, the autoinjector includes a protective cap to ensure that there are no accidental needle sticks. The force required to remove these caps is calibrated to ensure that any user, from a child to an arthritic senior, can easily remove it.

Autoinjectors rely on a needle shield that sheaths the needle until the device is pressed against the target injection site. Autoinjectors and pen injectors may be single-use devices and as such must be easy to dispose of safely.

In one aspect, medication dosing may be programmed onto the delivery device itself, ensuring that the desired dose, e.g., mass and/or volume, of the composition is delivered.

The time required to completely dispel the medicine into the body may be programmed into the autoinjector. For example, the ejection time may be 0.1 to 60, 0.5 to 30, 0.7 to 20, 0.8 to 10, 0.9 to 8, 1 to 7, 1.2 to 5, 1.5 to 4 seconds, or any time or interval in the recited ranges.

In some aspects, the syringe, autoinjector or injector pen provides one or more forms of feedback for the user indicating that the needle has been actuated and the medicine injected, e.g., audible or haptic feedback.

Figure 3:
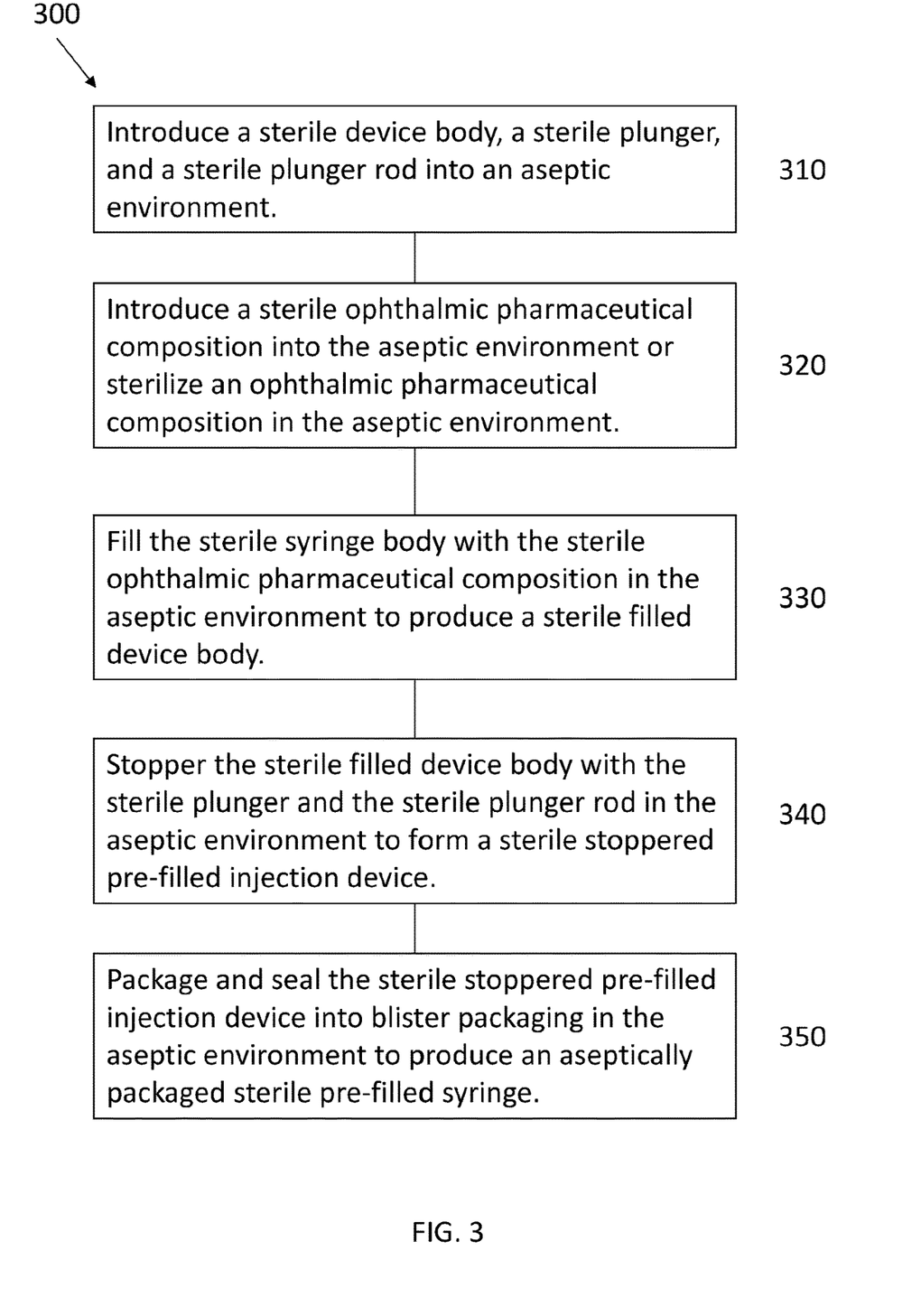
FIG. 3 shows an exemplary process for providing a packaged, pre-filled syringe in an aseptic environment, according to an embodiment of the present disclosure.

FIG. 3 shows an exemplary process 300 for providing a packaged, pre-filled syringe, according to an embodiment of the present disclosure. Process 300 is performed in one location, in an aseptic environment. In some examples, process 300 is performed by a person, by automatic, mechanical, or electronic equipment, or by a combination thereof.

In one aspect, the present disclosure includes packaging liquid products into containers in an aseptic environment. In some examples, the liquid products and containers are previously sterilized, prior to introduction in the aseptic environment. An aseptic environment provides conservation of sterility during the packaging of a liquid product into a container. For example, the present disclosure relies on an aseptic environment for filling a syringe with an ophthalmic solution and packaging the syringe.

In the aseptic environment, the surfaces that contact the packaged, pre-filled syringe and components thereof are configured to be non-reactive, non-additive, and non-absorptive. For examples, the surfaces are made with materials, which have non-reactive, non-additive, and non-absorptive properties when in contact with any of the components of the packaged, pre-filled syringe. Accordingly, the present disclosure avoids loss of costly therapeutic protein due to absorption/adsorption to the surfaces of the syringe.

In some examples, the aseptic environment comprises a sterile processing facility with an air filtration system. For example, the air filtration system is a positive pressure air filtration system which maintains a higher air pressure in the aseptic environment compared to an exterior of the aseptic environment. Consequently, contaminants will not flow into the aseptic environment even if the aseptic environment is not completely sealed.

In some examples, air supplies are filtered through high-efficiency particulate air filters, regardless of whether airflow is laminar or nonlaminar. In some examples, all entrances to the aseptic environment comprise a room of air showers. In some examples, the air filtration system provides an airflow in a single direction, in a robust and uniform manner, at a sufficient speed to reproducibly sweep undesired products away from the area in which process 300 is performed.

In some examples, the aseptic environment further includes pre-filters on water, gas, or steam supplies providing water, gas, or steam to the aseptic environment.

In some examples, the aseptic environment further includes aseptic processing systems for cleaning and disinfecting the environment and any equipment used.

Additional attributes of the disclosed aseptic environment can be as provided for by "Guidance For Industry Sterile Drug Products Produced by Aseptic Processing—Current Good Manufacturing Practice," U.S. Department of Health and Human Services Food and Drug Administration (September 2004), accessed at fda.gov/media/71026/download; "Facilities & Equipment CGMP Requirements" Regulatory Education for Industry (July 2015), accessed at fda.gov/media/92841/download; and Lehman, Christopher, "Sterile-grade filtration in pharmaceutical processing," Processing Magazine (March 2018), accessed at processingmagazine.com/home/article/15587323/steriligrade-filtration-in-pharmaceutical-processing, the contents of each of which are hereby incorporated by reference for all purposes.

Step 310 of process 300 provides for introducing a sterile syringe body, a sterile plunger, and a sterile plunger rod into an aseptic environment. For example, the aseptic environment includes any of the characteristics described above. For example, the sterile syringe body is syringe body 206 of FIG. 2, the sterile plunger is plunger 202 of FIG. 2, and the sterile plunger rod is plunger rod 204 of FIG. 2. In some examples, the sterile syringe body, the sterile plunger, and the sterile plunger rod are sterilized prior to step 310. In some examples, the sterile syringe body and the sterile plunger are silicone-free.

Step 320 provides for sterilizing an ophthalmic pharmaceutical composition. In some examples, the ophthalmic pharmaceutical composition is sterilized in the aseptic environment or before introduction into the aseptic environment. In some examples, step 320 provides for passing the ophthalmic pharmaceutical composition through an in-line sterile filter having a pore size of 0.45 microns or less, a pore size of 0.22 microns or less, or a pore size of 0.2 microns or less.

Step 330 provides for filling the sterile syringe body with the sterilized ophthalmic pharmaceutical composition in the aseptic environment to produce a sterile filled syringe body. For example, the ophthalmic pharmaceutical composition is poured into a plunger end 206*b* of syringe body 206 of FIG. 2. In some examples, the sterile syringe body is filled with the pharmaceutical composition using a pump, or another mechanical or electrical system.

Step 340 provides for stoppering the sterile filled syringe body with the sterile plunger and the sterile plunger rod in the aseptic environment to form a sterile stoppered pre-filled syringe. In some aspects, there is no air bubble between the ophthalmic pharmaceutical composition and the sterile plunger in the sterile syringe in step 340. In other aspects, an air bubble forms between the ophthalmic pharmaceutical composition and the sterile plunger in the sterile syringe body (e.g., air bubble 210 of FIG. 2) in step 340. In some aspects where the sterile syringe body and the sterile plunger are silicone free, step 340 provides for a sterile, stoppered, silicone-free, pre-filled syringe. In some examples, step 340 further provides for linking a needle or a cannula to an ejection end of the sterile stoppered pre-filled syringe body.

Step 350 provides for packaging and sealing the sterile stoppered pre-filled syringe into packaging in the aseptic environment to produce the aseptically packaged sterile pre-filled syringe. In some examples, the packaging is formed in the aseptic environment, e.g., thermoformed in the aseptic environment. In some examples, the packaging is formed outside of the aseptic environment, sterilized, and then introduced into the aseptic environment prior to step 350. In some examples, the packaging is a blister pack, a pouch, or a sealed wrapping.

In some examples, step 350 is performed directly after step 340.

In some examples, process 300 is performed by a worker wearing a clean and sterile garment. For example, the clean and sterile garment is disposable and/or is sterilized between uses. For example, the clean and sterile garment comprises a synthetic fabric constructed from non-woven filaments, and is at least one of: non-linting, anti-static, chemical resistant, non-flammable, and/or liquid-proof. In some examples, the synthetic fabric comprises at least one of polyester, Teflon laminated fabric, and/or Tyvek. In some examples, process 300 is performed robotically or by machines, with no human workers present in the environment during the process 300. Process 300 may be performed in an isolator system or a closed Restricted Access Barrier System (RABS) to further ensure an aseptic environment and to ensure that the composition, the dispenser, and the packaging are not exposed to viable organisms and particulate contamination. Such an environment may have an ISO Class 5/Grade A environment with unidirectional airflow enclosed in a rigid wall enclosure with glove port access where necessary. The interior of the enclosure is manually sanitized with sterilized equipment and parts introduced using aseptic procedures which can include transfer systems. The system may be located in an ISO Class 7/Grade C or better environment. Products or process contact parts within a RABS are sterilized or Steamed-In-Place (SIP) prior to use.

Closed RABS, like isolators, fully enclose and seal the work area, and supply the interior with HEPA filtered air that is returned through sealed ductwork. The interior of a closed RABS unit may be bio-decontaminated manually using cleaning solutions. Gowning may be for the ISO 7 or better environment. This can include the addition of full, sterile one-piece suits, sterile face masks, sterile head and shoe covers, goggles and multiple layers of gloves.

Isolators are fully enclosed and sealed units with HEPA filtered air supplied in a unidirectional manner to the ISO Class 5 interior. Completely closed isolators may be supplied with either turbulent air or unidirectional air. Air is typically recirculated by returning it to the air handlers though sealed ductwork. The chamber is bio-decontaminated via an automated cycle using $H_2O_2$ or another sanitant. All access is through glove ports and sterile transfer systems. All items entering the system after bio-decontamination are pre-sterilised. Because they are sealed, isolators are commonly located in ISO Class 8 environments. ISO 8 gowning is often comprised of items like a plant uniform or jumpsuit, lab coat, head cover and shoe covers. Single gloves are often used as a precaution during work using the isolator glove ports.

In some aspects, the enclosure is regularly tested and monitored to ensure the environment and a product formed in the environment meet aseptic requirements. An exemplary method is discussed further below regarding FIG. 4. Exemplary tests include (1) continuous passive air monitoring for microbes and particles; (2) surface swabs and/or touch plates in the aseptic area, which are tested during every production batch; (3) surface swabs and/or touch plates on personnel operating the aseptic area, which are tested during every production batch; (4) annual re-validation activities on process and equipment; (5) annual media fills to challenge personnel, process, and equipment; and/or (6) sterility testing per USP<71> for each product batch. USP<71> is incorporated herein by reference in its entirety. In some aspects, at least one of the foregoing tests is performed. In some aspects, at least two of the foregoing tests are performed. In some aspects, at least three of the foregoing tests are performed. In some aspects, at least four of the foregoing tests are performed. In some aspects, at least five of the foregoing tests is performed. In some aspects, all of the foregoing tests are performed.

In some aspects, sterility testing includes (1) testing the whole contents of an injection device in a product batch, (2) testing at least half the contents of an injection device in a product batch, where the volume tested is at least 1 mL, (3) in examples where the product batch of injection devices is 100 injection devices or less, testing the greater of 10% of the product batch or four injection devices; (4) in examples where the product batch of injection devices is greater than 100 injection devices but less than 500 injection devices, testing ten injection devices; (5) in examples where the product batch is greater than 500 articles, testing the lesser of 2% of the product batch or 20 injection devices. When the volume or the quantity in a single injection device is insufficient to carry out the tests, the contents of two or more injection devices are used to inoculate the different media. In certain aspects, test microorganisms may include one or more of *Staphylococcus aureus, Bacillus subtilis, Pseudomonas aeruginosa, Clostridium sporogenes, Candida albicans, Aspergillus niger, Micrococcus luteus* (*Kocuria rhizophila*), *Bacetroides vulgatus*.

In some aspects, sterility testing includes transferring the contents of the injection device to a culture medium and adding an inoculum of a small number of viable microorganisms (not more than 100 cfu) to the medium. In some aspects, a growth promotion test is performed as a positive control. All the containers containing medium are incubated for not more than 5 days. If clearly visible growth of microorganisms is obtained after the incubation, visually comparable to that in the control vessel without product, it can be determined that either the product possesses no antimicrobial activity under the conditions of the test or such activity has been satisfactorily eliminated. The test for sterility may then be carried out without further modification. If clearly visible growth is not obtained in the presence of the product to be tested, visually comparable to that in the control vessels without product, it can be determined that the product possesses antimicrobial activity that has not been satisfactorily eliminated under the conditions of the test. The sterility conditions of the aseptic environment are then modified in order to eliminate the antimicrobial activity, and the sterility testing is repeated. This method suitability is performed (a) when the test for sterility has to be carried out on a new product; and (b) whenever there is a change in the experimental conditions of the test.

In some aspects, where a needle or cannula is attached to the injection device, the needle or cannula is tested for sterility.

In some aspects, each batch of the packaged products is measured for bioburden levels. In some aspects, a selected set of samples from each batch is randomly swabbed inside the packaging and on the syringe surface to measure bioburden levels. In some aspects, measuring bioburden levels includes at least one of: (1) swabbing and plating (e.g., when testing bioburden levels for a hard to reach area in an aseptic environment); (2) direct contact plating (e.g., when testing bioburden levels for personnel or the floor in an aseptic area); (3) incubating and agitating a specific item from the aseptic environment in a growth promoting media to produce a liquid, and then using either (a) a membrane filter to capture microbes from the liquid and then incubating that filter on an agar plate or (b) directly pouring that liquid onto a plate and incubating (e.g., when testing bioburden levels for a specific object); (4) filtering a liquid obtained from the aseptic environment through a membrane filter to capture microbes and then incubating that filter on an agar plate or directly pouring a liquid onto a plate and incubating (e.g., when testing bioburden levels for a liquid such as an ophthalmic pharmaceutical formulation).

Therefore, process 300 provides several advantages over conventional methods of providing packaged, pre-filled syringes, as discussed above. For example, and without limitation, the disclosed process 300 occurs at a single location and requires less movement of the syringe between locations during packaging. These fewer movements reduce the opportunities for contamination. Additionally, the present disclosure provides for novel, aseptically-packaged, pre-filled syringes. Previous methods provided terminally sterilized, pre-filled syringes; however, the present disclosure further improves the quality of pre-filled syringes by aseptically packaging them and thereby avoiding the need for a terminal sterilization step. Pre-filled syringes in which the pharmaceutical is not degraded, destabilized, and contaminated are made according to the present disclosure. Such higher quality is especially important in syringes provided for ophthalmic injections because degradation products, aggregates, fragments, contaminants, and other non-desired molecules can lead to reduced efficacy, infection, severe pain, and/or blindness.

In some examples, the packaged, pre-filled syringe has a stopper slide force of less than 10N, 8N, 6N, or 4N. This low stopper slide force is the result of the coating of silicone oil on one or both of the outer circumferential surface of the sterile plunger and the inner circumferential surface of the sterile syringe body.

In some examples of method 300, the packaged, pre-filled syringe is configured to receive a sterile needle or sterile cannula to the stoppered pre-filled syringe.

In some aspects, the packaged, pre-filled syringe is configured to require less than 20, 15, 10, or 5 Newtons of force to eject the ophthalmic pharmaceutical composition from the syringe body when the sterile needle or sterile cannula is affixed thereto.

In certain aspects, the ejected the pharmaceutical composition is tested by a light obscuration procedure. In a light obscuration particle count test, the pharmaceutical composition will have 50 or fewer particles sized $\geq 10$ μm per mL and 5 or fewer particles sized $\geq 25$ μm per mL in accordance with USP 789 and USP 788, which are incorporated herein by reference in their entireties.

In certain aspects, the ejected the pharmaceutical composition is tested by a microscopic particle count procedure. In a microscopic particle count test, the pharmaceutical composition will have 50 or fewer particles sized $\geq 10$ μm per mL, 5 or fewer particles sized $\geq 25$ μm per mL, and 2 or fewer particles sized $\geq 50$ μm per mL in accordance with USP 789 and USP 788.

The present disclosure includes containers of ophthalmic preparations that are sterile at the time of filling and closing, and the container or kit or package is sealed such that the contents cannot be used without destroying the seal.

Figure 4:
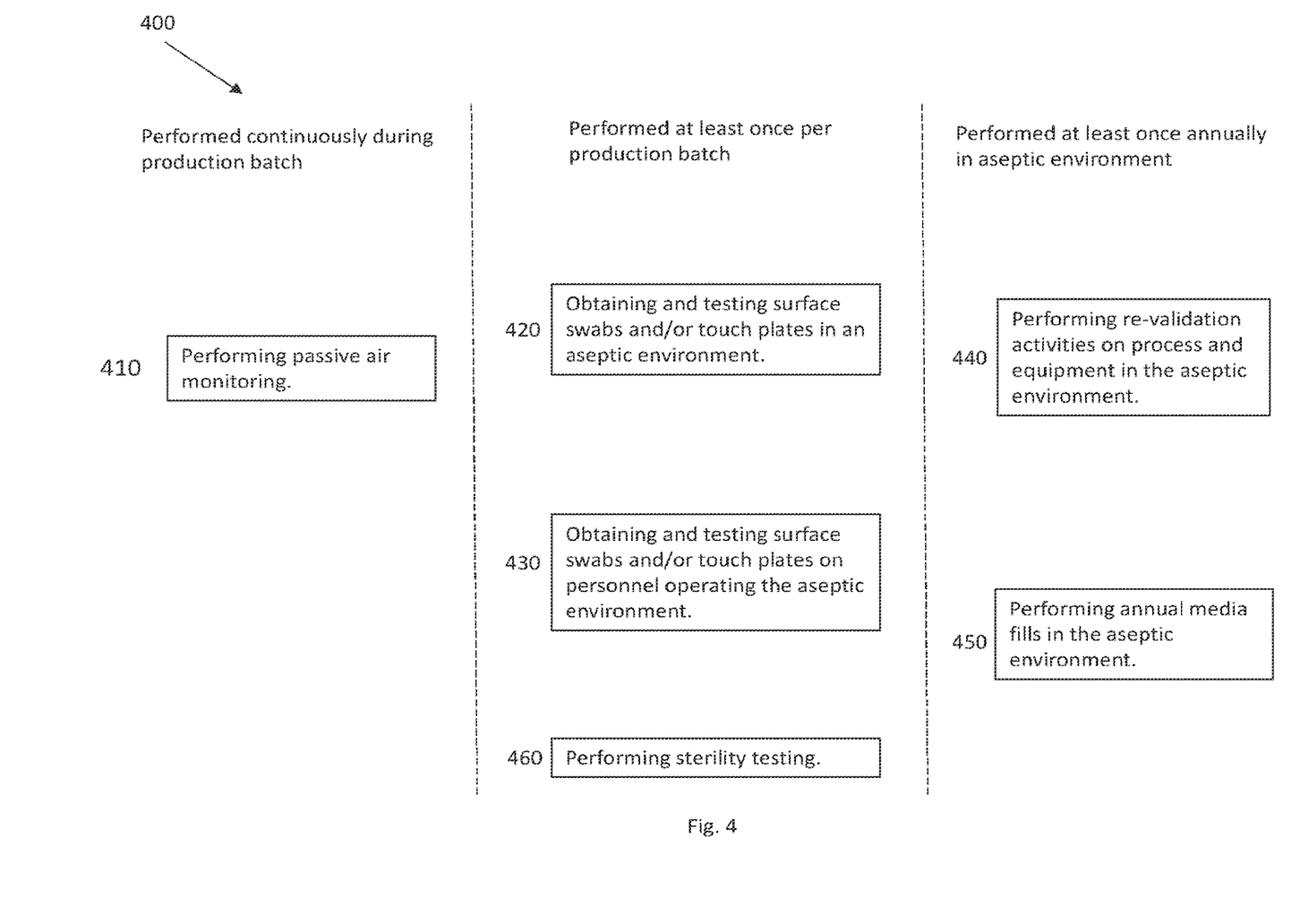
FIG. 4 shows an exemplary process for reproducibly validating a procedure for providing more than one production batch of aseptically-packaged sterile, pre-filled injection devices, according to an embodiment of the present disclosure.

FIG. 4 shows an exemplary process 400 for reproducibly validating a procedure for providing more than one production batch of aseptically-packaged sterile, pre-filled injection devices, according to an embodiment of the present disclosure. In some examples, process 400 is performed by a person, by automatic, mechanical, or electronic equipment, or by a combination thereof.

Process 400 includes a plurality of steps that can be performed in varying orders. Process 400 includes steps which are performed continuously during a production batch (e.g., step 410), steps which are performed at least once per production batch (e.g., steps 420, 430, and 460), and steps which are performed at least once annually in an aseptic environment (e.g., steps 440 and 450).

Step 410 of process 400 provides for performing continuous passive air monitoring for microbes and particles during the procedure for each production batch.

Step 420 provides for obtaining and testing surface swabs and/or touch plates in an aseptic environment at least once per production batch.

Step 430 provides for obtaining and testing surface swabs and/or touch plates on personnel operating the aseptic environment at least once per production batch.

Step 440 provides for performing re-validation activities on process and equipment in the aseptic environment at least once annually. For example, equipment in the aseptic environment with direct impact to sterilization is re-validated annually to ensure that the equipment remains in a validated state. For example, an autoclave in the aseptic environment may be revalidated to demonstrate that it can still achieve sufficient kill with a validated cycle. For example, a HEPA system may be re-validated to demonstrate that there are sufficient air exchanges. If positive pressure is used to separate areas of different environmental grades (e.g., inside a RABS versus outside a RABS), revalidation involving smoke studies may be performed to demonstrate unidirectional air flow.

Step 450 provides for performing annual media fills in the aseptic environment to validate personnel, process, and equipment. In some aspects, step 450 is used to validate that the personnel and procedures continuously and reproducibly produce sterile product with proper aseptic technique.

Step 460 provides for performing sterility testing according to USP<71> for each product batch.

Example 1

The following example provides a description of an exemplary study according to the present disclosure. The disclosed experiment verifies that syringes filled and placed into secondary packaging in an aseptic environment produces a prefilled syringe product that maintains sterility in its packaging.

The study has four different testing groups:
(1) Syringes filled with growth-promoting media and packaged in an aseptic environment, such as a hood or isolator;
(2) Syringes filled with growth-promoting media and packaged in a non-controlled environment, such as an exposed benchtop;
(3) Positive control: Syringes filled with growth-promoting media and packaged, where the media and the packaging are spiked a known quantity of microorganisms; and
(4) Negative control: Commercially available terminally sterilized prefilled syringe product, such as EYLEA™ (aflibercept) or LUCENTIS™ (ranibizumab).

All four groups will undergo a test procedure. First, the syringes will be incubated at a growth-promoting temperature (25° C.) for two weeks. After incubation, the solution in the syringes will be expelled and directly analyzed for microbial growth. Then, the syringe exterior surface and the packaging interior surface will be swabbed. Swabs will be used to plate any existing microorganisms onto a growth-promoting medium, such as an agar plate. Agar plates will be incubated at a growth-promoting temperature (25° C.) for two weeks and then any colony forming units will be counted.

Syringes filled with growth-promoting media and packaged in an aseptic environment, such as a hood or isolator are expected to have equal if not lower microbial growth compared to group (4), either in the solution expelled from the syringes, in the samples swabbed from the syringe exterior surface, in the samples swabbed from the packaging interior surface, or both. Groups (2) and (3) are expected to have significantly higher microbial growth compared to groups (1) and (4), either in the solution expelled from the syringes, in the samples swabbed from the syringe exterior surface, in the samples swabbed from the packaging interior surface, or both.

The expelled solution from Group (1) is expected to have zero CFU, or less than 10 CFU/100 mL. The swabs from Group (1) are expected to have zero CFU, or less than 10 CFU/100 mL.

Further, Group (1) is expected to satisfy a Sterility Assurance Level of $\leq 10^{-6}$.

While the subject matter of this disclosure has been described and shown in considerable detail with reference to certain illustrative aspects, including various combinations and sub-combinations of features, those skilled in the art will readily appreciate other aspects and variations and modifications thereof as encompassed within the scope of the present disclosure. Moreover, the descriptions of such aspects, combinations, and sub-combinations is not intended to convey that the claimed subject matter requires features or combinations of features other than those expressly recited in the claims. Accordingly, the scope of this disclosure is intended to include all modifications and variations encompassed within the spirit and scope of the following appended claims.

What is claimed is:

1. A method for providing an aseptically-packaged sterile, pre-filled injection device, comprising:
introducing a sterile device body, a sterile plunger, and a sterile plunger rod into an aseptic environment;
introducing a sterile ophthalmic pharmaceutical composition into the aseptic environment or sterilizing an ophthalmic pharmaceutical composition in the aseptic environment;
filling the sterile device body with the sterile ophthalmic pharmaceutical composition in the aseptic environment to produce a sterile filled device body;
stoppering the sterile filled device body with the sterile plunger and the sterile plunger rod in the aseptic environment to form a sterile stoppered pre-filled injection device; and
packaging and sealing the sterile stoppered pre-filled injection device into packaging in the aseptic environment to produce the aseptically packaged sterile pre-filled injection device.

2. The method of claim 1, wherein the packaging is thermoformed in the aseptic environment.

3. The method of claim 1, comprising sterilizing the packaging and then introducing the sterilized packaging into the aseptic environment prior to the packaging step.

4. The method of claim 1, wherein sterilizing the ophthalmic pharmaceutical composition in the aseptic environment comprises passing the ophthalmic pharmaceutical composition through an in-line sterile filter having a pore size of 0.22 micron or less.

5. The method of claim 1, wherein the packaging and sealing step is performed directly after the stoppering step.

6. The method of claim 1, wherein the aseptically packaged sterile pre-filled injection device is not subjected to a terminal sterilization step.

7. The method of claim 1, wherein the aseptic environment comprises a sterile processing facility with a positive pressure air filtration system.

8. The method of claim 1, wherein the introducing step, the sterilizing step, the filling step, the stoppering step, and the packaging and sealing step are performed by a worker wearing a clean and sterile garment.

9. The method of claim 8, wherein the clean and sterile garment is disposable or wherein the clean and sterile garment is sterilized between uses.

10. The method of claim 8, wherein the clean and sterile garment comprises a synthetic fabric constructed from nonwoven filaments, and is at least one of: non-linting, antistatic, chemical resistant, non-flammable, and/or liquid-proof, optionally wherein the synthetic fabric comprises at least one of polyester, Teflon laminated fabric, and/or Tyvek.

11. The method of claim 1, further comprising affixing a cap to the syringe before the filling step.

12. The method of claim 1, wherein the ophthalmic pharmaceutical composition comprises a VEGF antagonist, optionally wherein the VEGF antagonist is ranibizumab or aflibercept.

13. The method of claim 1, wherein at least one of the sterile device body, sterile plunger, or sterile plunger rod is sterilized by treatment with ethylene oxide prior to the introducing step.

14. The method of claim 1, wherein at least one of the sterile device body, sterile plunger, or sterile plunger rod is sterilized by treatment with steam prior to the introducing step or wherein at least one of the sterile device body, sterile plunger, or sterile plunger rod is sterilized by treatment with radiation prior to the introducing step.

15. The method of claim 1, wherein the pre-filled injection device is a pre-filled syringe and wherein the device body is a syringe body.

16. The method of claim 1, wherein the packaging comprises blister packaging or is a pouch.

17. The method of claim 7, wherein the sterile processing facility is a Restricted Access Barrier System with an ISO rating of Class 5 or higher.

18. The method of claim 1, wherein at least one step selected from the group consisting of the introducing step, the sterilizing step, the filling step, the stoppering step, and the packaging and sealing step is performed robotically.

19. The method of claim 17, wherein the sterile processing facility is a Restricted Access Barrier System with an ISO rating of Class 7 or higher.

20. The method of claim 7, wherein the sterile processing facility is an isolator with an ISO rating of Class 8.

21. The method of claim 1, wherein introducing the sterile ophthalmic pharmaceutical composition into the aseptic environment comprises filter sterilizing the ophthalmic pharmaceutical composition into a sterile bag outside of the aseptic environment and then introducing the sterile bag containing the sterile ophthalmic pharmaceutical composition into the aseptic environment.

22. The method of claim 1, further comprising measuring the aseptically packaged sterile pre-filled injection device for bioburden levels.

23. The method of claim 22, wherein the bioburden levels are measured by swabbing a surface in the aseptic environment and plating the swab on a growth media to measure bacterial growth on the growth media, or
wherein the bioburden levels are measured by direct contact plating a growth media to measure bacterial growth on the growth media, or
wherein the bioburden levels are measured by incubating and agitating an item from the aseptic environment in a growth promoting media to form a liquid, and then either (i) using a membrane filter to capture microbes from the liquid and then incubating that membrane filter on an agar plate or (ii) directly pouring the liquid onto an agar plate and incubating, or
wherein the bioburden levels are measured by obtaining a liquid sample from the aseptic environment, and then either (i) using a membrane filter to capture microbes from the liquid and then incubating that membrane filter on an agar plate or (ii) directly pouring the liquid onto an agar plate and incubating,
optionally wherein the liquid is an ophthalmic pharmaceutical formulation.

24. A method of reproducibly validating a procedure for providing more than one production batch of aseptically-packaged sterile, pre-filled injection devices, comprising performing at least one of the following steps:
(1) performing continuous passive air monitoring for microbes and particles during the procedure for each production batch;
(2) obtaining and testing surface swabs and/or touch plates in an aseptic environment at least once per production batch;

(3) obtaining and testing surface swabs and/or touch plates on personnel operating the aseptic environment at least once per production batch;

(4) performing re-validation activities on process and equipment in the aseptic environment at least once annually;

(5) performing annual media fills in the aseptic environment to validate personnel, process, and equipment; and (6) performing sterility testing according to USP<71> for each product batch.

25. The method of claim 24, wherein the sterility testing comprises testing the whole contents of a packaged sterile pre-filled injection device in the production batch.

26. The method of claim 24, wherein the sterility testing comprises performing a growth promotion test on the contents of the packaged sterile pre-filled injection device.

27. The method of claim 24, wherein the re-validation activities comprise revalidating equipment with direct impact to sterilization in the aseptic environment.

28. The method of claim 27, wherein the equipment is an autoclave and the revalidating step comprises confirming that the autoclave achieves a predetermined kill rate in a validation sample that is subjected to a validation cycle in the autoclave, or wherein the equipment is a HEPA system and the revalidating step comprises confirming that the HEPA system performs a predetermined number of air exchanges during a validation cycle, or wherein the equipment is a positive pressure system used to separate areas of different environmental grades and the revalidating step comprises confirming unidirectional air flow by performing a smoke study.

\* \* \* \* \*